United States Patent [19]

Baldwin

[11] Patent Number: 5,354,984

[45] Date of Patent: Oct. 11, 1994

[54] GLASS CONTAINER INSPECTION MACHINE HAVING MEANS FOR DEFINING THE CENTER AND REMAPPING THE ACQUIRED IMAGE

[75] Inventor: Leo B. Baldwin, Horseheads, N.Y.

[73] Assignee: Emhart Glass Machinery Investments Inc., Wilmington, Del.

[21] Appl. No.: 116,664

[22] Filed: Sep. 3, 1993

[51] Int. Cl.$^5$ ............................................. G01N 9/04
[52] U.S. Cl. ............................ 250/223 B; 356/240; 382/8
[58] Field of Search ................... 250/223 B, 223 R; 356/240, 237, 372; 382/8, 1, 41, 42, 54; 209/939

[56] References Cited

U.S. PATENT DOCUMENTS 4,608,709  8/1986  Hedler et al. ........................ 382/1
5,095,204  3/1992  Novini ............................. 250/223 B Primary Examiner—David C. Nelms
Assistant Examiner—Que T. Le
Attorney, Agent, or Firm—Spencer T. Smith

[57] ABSTRACT

An inspection machine for inspecting the circumference of a vertically standing container comprising means for conveying a vertically standing container through an inspection location including means for directing a beam of collimated light vertically downwardly towards the container, the beam having a configuration selected so that when the container is located at the inspection location the periphery of the beam will be spaced from the circumference of the container, two dimensional camera means for axially viewing the profile of the vertical projection of a container at the inspection location, and image processing means for evaluating the circumference of the profile viewed by the two dimensional camera and accepting or rejecting the container including means for defining the center of the acquired image, and means for remapping the perimeter of the acquired image into at least one two-dimensional rectangular area bisected by an imaginary line representing the perimeter of an ideal container in vertical projection.

5 Claims, 3 Drawing Sheets

GLASS CONTAINER INSPECTION MACHINE HAVING MEANS FOR DEFINING THE CENTER AND REMAPPING THE ACQUIRED IMAGE

The present invention relates to the inspection of cylindrical glass ware for malformations, dimensional variations and defects.

Glass containers are conventionally produced in an I.S. (individual section) machine from discrete gobs of molten glass. Each gob is first operated on in a blank mold, which has opposed side portions to form a parison and then the parison is blown into the finished container in a blow mold which also has opposed side portions. The container should have the desired shape (cross section). Where the overall variation from this shape is excessive, the container should be rejected. Where these opposed side portions of the blow mold come together a bottle seam will be formed and can usually be observed in the formed container. This seam (a local variation) can be unacceptably noticeable or a thin "fin" of glass can be formed at the seam and extend partially or completely along the seam. In either case, the container should be rejected upon inspection.

It is an object of the present invention to provide an improved algorithm for inspecting the exterior dimensions of glass bottles.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings.

Figure 1:
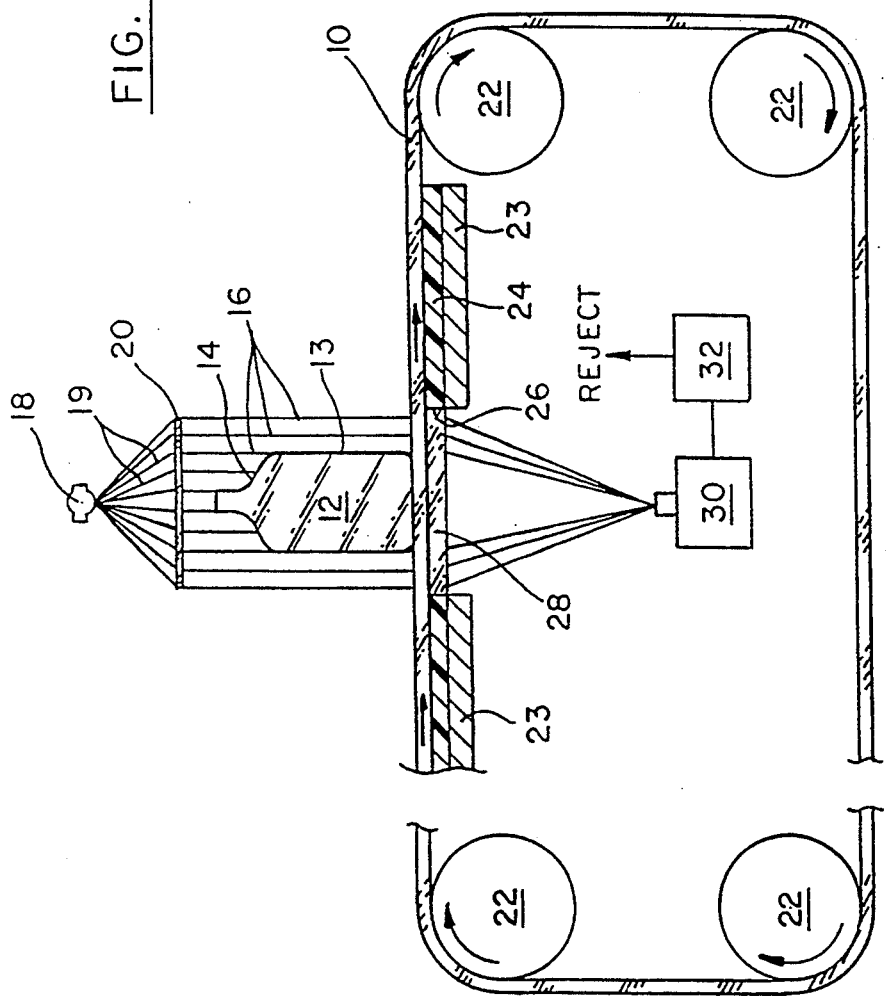
FIG. 1 is a schematic showing of a conventional machine for inspecting the periphery (shape) of a cylindrical glass container.
Figure 2:
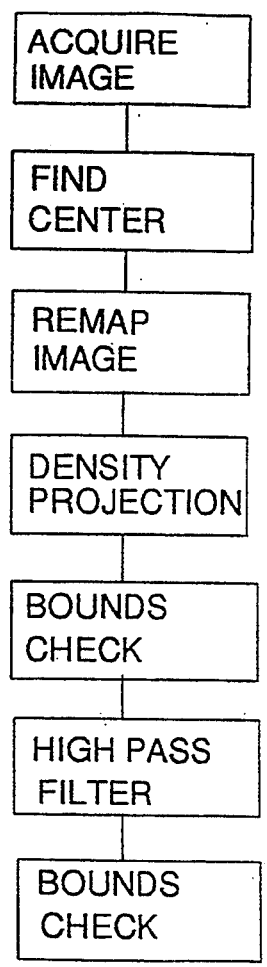
FIG. 2 is a flow chart of the inspection algorithm.
Figure 3:
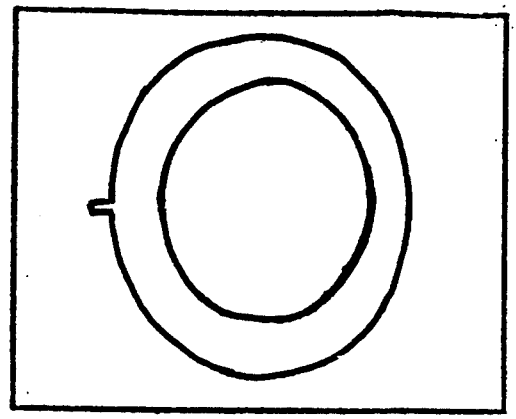
FIG. 3 is a view representing the bottle shown in FIG. 1, as seen by the camera.

The inspecting machine has a conveyor 10 onto which containers 12 are deposited by a feeder (not shown). Each container has a cylindrical (circular or elliptical, for example) form 13 extending vertically from the bottom of the bottle upwardly to the neck portion 14 (the axis of the bottle is vertical). The conveyor moves continuously and during its displacement the container becomes located at the illustrated inspection location where collimated light 16 passes vertically downwardly over the container. A Fresnel lens 20 receives light 19 dispersing from a short arc flash tube 18 to form the collimated light beam 16. As shown in FIGS. 2 and 3, the footprint of the collimated beam on the conveyor is selected so that for any conveyed bottle, an annular band of light will surround the bottle.

The conveyor is a one-piece, seamless, belt cast from transparent urethane and is driven by a drive system 22. It is supported by a metallic plate 23 which is covered with Teflon® 24. Flush with the surface of the strip and secured within an opening 26, is a diffuser plate 28. A two-dimensional camera 30 viewing vertically upwardly views the profile of the vertical projection of the container through the diffuser plate and sees the collimated light footprint. The sensed image is evaluated by an image processing computer 32. Such an image processing computer will evaluate the shape or circumference (or outline, perimeter, outside edge, edge) of the image of the bottle as cast onto the diffusing surface by the collimated beam as shown in FIG. 2 and determine the presence of a fin 34 (FIG. 2) or an unacceptable out of round shape. The computer can then issue a signal to reject the bottle. The inspected container will then leave the conveyor for further processing by structure not shown.

Figure 4:
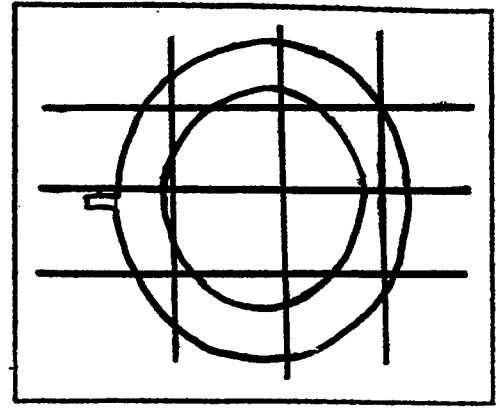
FIG. 4 is a view similar to that of FIG. 3 illustrating how the center of the image is detected.

FIG. 2 is a flow chart of the inventive algorithm. The first block (acquire image) is represented by the screen shown in FIG. 3 which is the image of the bottle on the CRT screen (the image stored in the memory space of the digital image processing device). The next step is to find the center of that image. As shown in FIG. 4, x and y chords are scanned to locate the transition point (the location where light changes to dark, indicating the edge of the image) and then the complementary transition point (the location where dark changes to light, indicating the other edge of the image). The stored image is of a spatial resolution sufficiently high to insure the required measurement accuracy and sufficient amplitude resolution to insure that the projected image can be distinguished from its background. With these two points, a mid x and mid y location (the x,y center point) can be determined (a voting procedure can be used to throw out bad data). This center point could also be assumed or located with other techniques such as with a bounding box, for example. Where the image is non-round (elliptical, for example) the orientation will also be determined.

Figure 5:
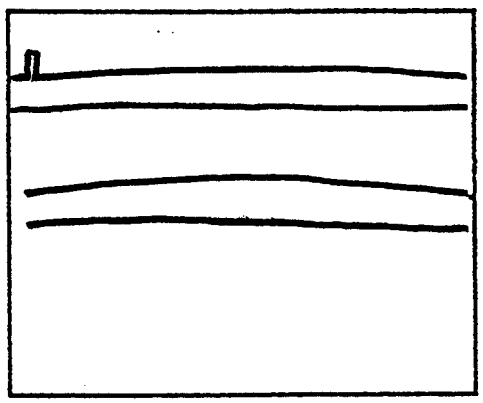
FIGS. 5-9 are frames illustrating the other steps of the algorithm.

An area which includes the perimeter edge of the image is then remapped, as shown in FIG. 5, into another digital memory space such that the ideal bottle perimeter would lie on one or more straight line segments (a function of the length of the perimeter). This can be done with any imaging processing system which includes a pixel re sampler or warper device for spatial transformations, or the remapping can be done in software. In the case of the illustrated image for a nominally round bottle, this area is annular with the minor radius somewhat less than the radius of the image of the bottle projection and the major radius somewhat more. The shape of the area to be remapped in the source frame will always be representative of the shape of the bottle in its vertical projection, and the shape of the area into which the source area is remapped is always one or more rectangular areas, bisected along one axis by the (imaginary) straight line representing the perimeter of the ideal bottle in vertical projection. In general, the pixel area of the source image area will be preserved in the remapping as well as the general spatial relationships between images. This operation is known within the art as "warping" of the image, and is a discreet implementation of the geometric operation known as conformal mapping. The warping may be done with or without interpolation.

Figure 6:
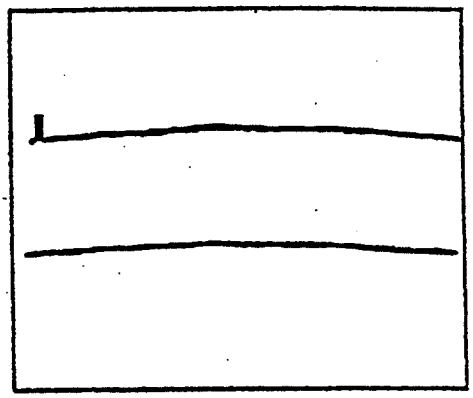
Figure 7:
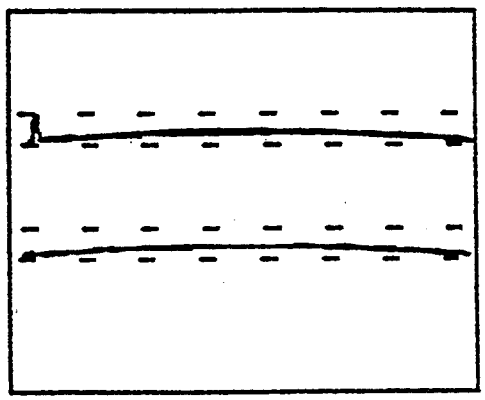

The two-dimensional array representation of the perimeter of the bottle image in vertical projection is next reduced to a one-dimensional array representation in a step called density projection. In the example, the edge of the bottle image has been remapped into a plurality of horizontal images. By summing vertically along the pixel columns, this two-dimensional array of numbers can be reduced to a one-dimensional array of numbers (FIG. 6), whereby each number represents the local difference in radius as measured in pixel units from the inside boundary of the source area used in the warping operation. Note that if the bottle image boundary had been remapped into a plurality of vertical rectangles, these rectangles would be summed horizontally along the pixel rows and the operation would be equivalent.

In the next operation (bounds check), the one-dimensional arrays of numbers are checked to make sure they fall within bounds directly or indirectly set by the operator. In general, this bound will be set by the operator indirectly as the maximum and minimum acceptable dimensions of the bottle in the vertical projection view, such as may be taken from a blueprint of the bottle in its vertical projection. The computing device will, in this case, during setup, and considering other factors such as pixel, dimensions and optical magnification, convert these dimensional tolerances to the upper and lower bounds used to filter the one dimensional arrays for unacceptable variations in shape. Optionally, this bounds check can be performed on the two-dimensional area shown in FIG. 5.

There is a second category of defect to be analyzed, and that is the highly localized variation in shape, a primary example of which is the "fin" which results when glass is erroneously pressed into the seam which separates the two halves of the mold into which the molten glass is blown to give its final shape. These projections are unacceptable in dimensions which may be acceptable for overall variations in shape. Furthermore, a localized protrusion may exist in an area which is overall undersized by an acceptable amount, such that the overall undersized geometry masks the local protrusion if simple bounds checking is applied as in FIG. 5. This would happen where the area containing the fin has also caved in slightly. The amount of the cave in may be acceptable, but it can cause the fin to lie within acceptable limits. The fin is, however, unacceptable and the inspection system must recognize it as such.

The function of the high pass filter (FIG. 6) is to eliminate the overall variations in shape from the one-dimensional array representation while leaving the representation of local variations intact or even increasing their local magnitude. This is done by comparing each pixel to its immediate neighborhood as follows: a pixel P in the array is denoted by subscript n. The pixel preceding it is subscripted n−1 and the pixel following it is subscripted n+1. Pixel Pn is remapped to a second array, denoted P′, called "P primed." Pixel $P'_n$ is calculated from the original array as:

$$P'_n = P_n \times 2 - P_{n-1} - P_{n+1}$$

Figure 8:
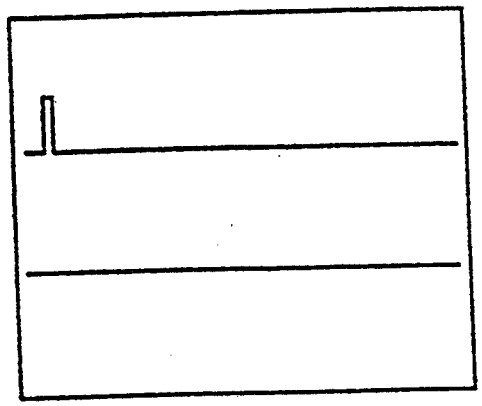
Figure 9:
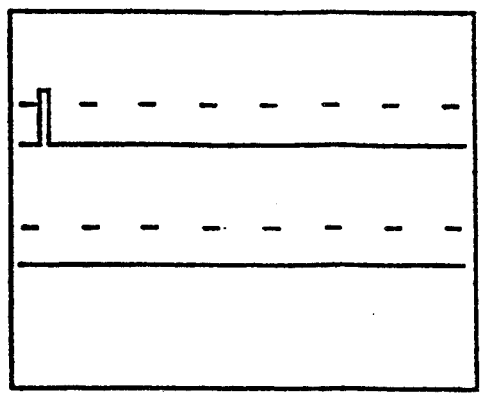

Note that if $P_n$, $P_n-1$ and $P_n+1$ all have the same value, then the value of $P'_n{}'$ is zero. If it is larger than its neighbors, then this difference is exaggerated. Every pixel in the source array is remapped to the primed array in this way. This mapping is represented in FIG. 8. Note that the gradual fluctuations in diameter have been suppressed while the localized fluctuation, the fin, has been enhanced. This operation is known in the art as a high pass filter, or more generically a finite impulse response filter (FIR filter), which may be configured to do the opposite operation, a low pass filter. It is commonly implemented as a convolution. Note that a greater number of neighbors may be considered in this operation, such as two pixels before and two pixels after. A bounds check (FIG. 9) is then performed for these fins.

I claim:

1. An inspection machine for inspecting the circumference of a vertically standing container comprising
   means for conveying a vertically standing container through an inspection location including
   means for directing a beam of collimated light vertically downwardly towards the container, said beam having a configuration selected so that when the container is located at the inspection location the periphery of said beam will be spaced from the circumference of the container,
   two dimensional camera means for axially viewing the profile of the vertical projection of a container at the inspection location, and
   image processing means for evaluating the circumference of the profile viewed by said two dimensional camera including
   means for defining the center of the acquired image, and
   means for remapping the perimeter of the acquired image into at least one two-dimensional rectangular area bisected by an imaginary line representing the perimeter of an ideal container in vertical projection.

2. An inspection machine according to claim 1, further comprising
   means for bound checking each of said two-dimensional rectangular areas.

3. An inspection machine according to claim 1, further comprising
   means for projecting each of said two-dimensional rectangular areas into a one dimensional array whereby, the magnitude of each element of the array represents the local variation in container radius at the location on the perimeter represented by the index of the array element, and
   means for bound checking each of said one-dimensional arrays.

4. An inspection machine according to claim 3, further comprising
   a high spatial frequency filter for filtering each of said one-dimensional arrays, and
   means for bound checking each of said filtered arrays to detect local variation in container geometry.

5. An inspection machine according to claim 1, further comprising
   means for projecting each of said two-dimensional rectangular areas into a one dimensional array whereby, the magnitude of each element of the array represents the local variation in container radius at the location on the perimeter represented by the index of the array element,
   a high spatial frequency filter for filtering each of said one-dimensional arrays, and
   means for bound checking each of said filtered arrays to detect local variation in container geometry.

* * * * *